United States Patent
Schrøder et al.

(10) Patent No.: US 6,875,337 B1
(45) Date of Patent: Apr. 5, 2005

(54) METHOD AND MEANS FOR PERFORMING ELECTROCHEMICAL ANALYSIS

(76) Inventors: Knut H. Schrøder, Vilhelm Krags vei 2, N-7023 Trondheim (NO); Øyvind Mikkelsen, Myrsnipeveien 20, N-7082 Kattem (NO)

( * ) Notice: Subject to any disclaimer, the term of this patent is extended or adjusted under 35 U.S.C. 154(b) by 0 days.

(21) Appl. No.: 09/958,663
(22) PCT Filed: Apr. 14, 2000
(86) PCT No.: PCT/NO00/00124
§ 371 (c)(1), (2), (4) Date: Jan. 8, 2002
(87) PCT Pub. No.: WO00/63686
PCT Pub. Date: Oct. 26, 2000

(30) Foreign Application Priority Data

Apr. 16, 1999 (NO) .......................................... 19991814

(51) Int. Cl.[7] ............................................. G01N 27/403
(52) U.S. Cl. ..................... 205/789.5; 204/416; 205/775
(58) Field of Search .............................. 205/789.5, 775, 205/777.5, 787–789, 792–794; 73/1.83, 64.53, 632, 661; 204/400, 403.01, 403.14, 404, 405, 406, 409, 412, 415, 416

(56) References Cited

U.S. PATENT DOCUMENTS 4,201,646 A 5/1980 Matson ........................ 204/406
5,384,029 A 1/1995 Campbell ..................... 204/415

FOREIGN PATENT DOCUMENTS

SU 1249429 A 8/1986 .......... G01N/27/46

OTHER PUBLICATIONS

Bratten et al. ("Micromachining sensors for Electrochemical Measurement in Subnanoliter Volumes," Anal. Chem. 1997, 69, 253–258).*

* cited by examiner

Primary Examiner—Alex Noguerola
(74) Attorney, Agent, or Firm—Wenderoth, Lind & Ponack, L.L.P.

(57) ABSTRACT

The present invention concerns a method for improving the sensitivity in measurements when performing electrochemical analysis containing low metal concentrations and a means for performing electrochemical analysis. Ordinary stirring has to be avoided during the voltammetric scanning due to the low reproducibility when stirring takes place. A sound exposure, however, can be performed during the entire measurement, increasing the sensitivity. Further it is concluded that sound exposure close to the resonant frequency, has improvement effects at least comparable to stirring, and thus all mechanical stirring can be avoided. It is found that audible sound in the low frequency range, around 100 Hz is very effective for this purpose, with an increase of the analytical signal up to about 300%, without any significant increase in the corresponding noise level.

20 Claims, 5 Drawing Sheets

METHOD AND MEANS FOR PERFORMING ELECTROCHEMICAL ANALYSIS

This application is the national stage under 35 U.S.C. § 371 of PCT/NO00/00124, filed 14 Apr. 2000.

FIELD OF THE INVENTION

The present invention concerns a method for increasing sensitivity in measurements when performing electrochemical analysis and means for performing electrochemical analysis. Uses of the method and the means am also presented.

BACKGROUND OF THE INVENTION

Voltammetry is a group of electroanatytical methods where one achieves a current signal due to a redox reaction at a given potential. The current is controlled by the mass which diffuses to the electrode surface and there is a linear relation between signal and concentration of the analyte.

Various voltammetric methods are important in the determination of compounds in trace levels, with the additional advantage that it can be used not only to determine the total content, but this can also be used for speciation studies in the environment [1–3].

In general, however, direct voltammetric methods are not always sufficiently sensitive to allow trace determinations of pollutants like heavy metals and pesticides. However, the use of different pulse techniques are well known procedures to increase the sensitivity, but even higher sensitivity is required for trace determinations in natural surroundings. One way to increase the sensitivity is to preconcentrate the actual sample. Using various stripping techniques can perform this, and such methods will not normally contaminate the sample. Another way of increasing the signal is to modulate the voltammetric curve with alternating current or potential pulses, or by combining the most appropriate of the above mentioned techniques, like in differential pulse stripping voltammetry, with satisfactory results. However, one problem has to be considered. The increase in sensitivity is only interesting if the noise level is not increased accordingly.

Differential pulse anodic stripping voltammetry (DPASV) is an electrochemical method of analysis where one achieves especially good sensitivity as a result of a combination of a preconcentration step and an advanced measuring procedure which gives a favourable signal-to-noise ratio. The preconcentration is performed by holding the working electrode at a negative potential, then reducing metal ions from the solution to amalgam on a mercury electrode. The metal is preconcentrated into the electrode by a factor of 100 to 1000, and one may determine four to six metals simultaneously in mixtures with concentrations down to $10^{-10}$ M.

During the preconcentration step the solution is stirred to improve the mass transport to the electrode surface. The mechanical stirring has two major effects: 1) mechanical transport of ions to the electrode, 2) reducing the thickness of the diffusion layer. The diffusion layer is the area close to the electrode where the concentration of the actual species is lower than the concentration in the bulk of the solution, due to the electrode process. Diffusion is a slow and controlling process and one therefore wishes to lower the diffusion layer to achieve an increased mass transport to the electrode surface where the redox reaction is taking place.

Stirring of a solution in connection with voltammetric measurements, like in DPASV, will give an increase in signal. This is due to the fact that mass transport to the electrode will be facilitated, corresponding to an effective decrease of the thickness of the diffusion layer. But on the other hand, stirring (e.g. with a magnetic stirrer) will be unfavourable for the reproducibility thus being carried out during the preconcentration step only, and normally skipped during the registration of the signal.

The concentration gradient formed close to the surface of the electrode lowers the surface concentration of the actual species. The use of a magnetic stirrer is a well-known technique, by diffusion layer thinning, to increase the surface concentration.

Several techniques have been introduced recently in order to improve the sensitivity and reproducibility of various voltammetric methods of analyses. Among such techniques, rotating electrodes are frequently used [4–7]. Here the rotation has the similar effect an sensitivity as stirring, but being much more reproducible. Some voltammetric experiments with rotating electrodes are reported using stirring during the entire measurement cycles, but normally such investigations are carried out with unstirred or unrotated conditions during the scanning step in order to achieve optimum reproducibility [8, 9]. Other techniques [10–21] have also been introduced to increase the sensitivity and applicability of voltammetric analyses. Of great importance is the use of chemical modified electrodes [22–24]. The application of microelectrodes and ultramicroelectrodes is also an important field in order to improve the detection limit and to allow new applications of the analytical method [25, 26]. Other recent developments are the flow sensor electrode [27–29] and the introduction of the band array microelectrode [30).

The application of ultrasound in voltammetry is a well-established technique [31–39], and a field in fast development. The favourable effects by using ultrasound is mainly due to the following: Increased mass transport of the redox species to the surface of the electrode, an efficient and continuous cleaning of the electrode surface, degassing of the electrode surface, and a removal of a possible viscous surface layer on the electrode.

Another reason for using ultrasound in electroanalytical methods is the fact that high-energy ultrasound can activate the actual compounds, and the chemical reactions, through the acoustic cavitation or through acoustic streaming.

There are several physical mechanisms occurring by using ultrasound which can modify the process, e.g. creation of ions, radicals and other intermediate products rich in energy as a consequence of transient cavitation, ultrasonic activation of chemical processes associated with electron transport in steps, continuous cleaning and activation of electrode surfaces, and an increased mass transport as a result of cavitation in the solution. The purpose of using ultrasound in connection with electrochemical analysis are the effects that follow from cavitation.

Cavitation is a phenomenon that occurs for high frequency sound. Small gas bubbles are created in the medium which then collapse and disengages large amounts of energy. There are theories assuming that the temperature locally may reach 5000 K and that the pressure locally may reach a level of several thousands atmospheres for a short time when the bubbles collapse. The bubbles are created and destroyed by the extremely powerful oscillations in the medium. Ultrasound causes the molecules in the medium to stretch far and fast apart beyond the limit of the critical distance that keep the molecules together. The molecules are torn apart and gas bubbles are created. When the medium oscillates back, the bubbles are compressed, and collapse. The high energy and high pressure that follows from a bubble collapse give the special properties to the chemical elements in the medium.

As a summary, in ultrasound exposed analysis the technique is to use the phenomenon of cavitation to reduce the thickness of the diffusion layer, and in this way increasing the mass transport to the electrode surfaces. However, when using ultrasound one has to use a magnetic stirrer for performing the mechanical transport to the diffusion layer.

The fact that rotating electrodes, at least partially, can be kept rotating during the voltammetric scanning, focused on using alternative ways of reproducible mass transport to the electrode.

SUMMARY OF THE INVENTION

Our laboratory experiments have been carried out in order to substitute stirring with sound exposure. Differential pulse anodic stripping voltammetry (DPASV) of heavy metals was selected as the method for the present experiments, other voltammetric techniques like cyclic voltammetry, differential pulse polarography, AC polarography are assumed to behave accordingly, but this will be investigated later after optimum conditions are found for DPASV. This also includes studies of the effect of audible sound using microelectrode systems.

The purpose of the present invention is to utilize the effects of low frequency sound, standing waves and resonance in order to find if the transport of mass (e.g. thinning of the diffusion layer) will give analytical improvements in stripping voltammetry compared with the well established use of a magnetic stirrer.

According to the knowledge of the inventors, voltammetry with modulation with audible sound has not been investigated previously. By using the new possibilities arising from the multimedia development in computer equipment, it might be possible to improve the analytical use of voltammetry by exposing the electrode system with sound at audible frequencies. This is investigated in the present application.

The object of the present invention is to replace the present stirring techniques in all electrochemical analysis techniques with a reliable, simple technique that improves reproducibility and increases the sensitivity without increasing the noise level. This has surprisingly proven to be the case when introducing low frequency audible sound waves into the analysis cell. In that frequency range, cavitation effects are assumed not to be present and increased sensitivity without corresponding increase of the noise level is postulated.

Audible sound has a frequency from about 20 Hz to about 20 000 Hz and propagates in the form of longitudinal waves. Due to the elasticity of the medium, the presence of the waves makes regions with different pressures and densities in the medium. This makes streaming effects, somewhat related to conventional stirring [40]. The formation of a concentration gradient as a consequence of diffusion will implicate that the concentration decreases towards the electrode. But when the system is continually exposed to audible sound the areas with different densities will be maintained and the high concentration preserved. In this way the formation of a concentration gradient is opposed. Consequently, a high concentration of the analyte may be upheld during the whole analysis, giving a better sensitivity.

The areas with different densities created during audible sound exposure changes the properties of the medium. Changes in density or pressure will probably influence the forces between the medium and the electrode surface. An additional effect is therefore that sound exposure possibly might change the structure of the electrical double layer. Consequently also by changing the redox properties of the system.

Of particular importance are the effects of standing waves and resonance. When sound waves propagate in a fluid in a pipe with finite length, the waves are reflected from the ends in the same way that transverse waves on a string are reflected at its ends. The superposition of the waves travelling in opposite directions again forms a standing wave, which is a steady-state condition resulting in periodically fields with higher and lower densities than normal conditions [41].

Resonance can occur in mechanical, structural, and acoustical systems. If a system is excited by the continued application of external forces at the natural frequency, which is the frequency at which the system would vibrate if deflected once and then allowed to move freely, then the amplitudes of the oscillation will build up and result in strong vibration of the medium and in some cases structural destruction. In this way it is possible to put the analysis system into resonance and achieve a "shaking effect" in the system. It is also possible to put an electrode into resonance thereby causing a reduction in the diffusion layer.

In stripping analysis one may cut the deposition time used to deposit the analyte. Using low frequency audible sound one may deposit material and simultaneously measuring. The sound gives a reproducible mass transport which can be utilized during the measurement sequence. This can not be performed by a magnetic stirrer, as it creates a lot of noise, or by using ultrasound.

Low frequency audible sound contributes to electroanalytic measurements through increased mechanical mass transport towards the electrode and a reduction of the diffusion layer, thereby increasing mass deposition. When using low frequency audible sound the physical vibration introduced to the medium by the sound waves is utilized. This effect especially appears at resonance, a state which can not be attained by ultrasound.

The geometric shape of the analysis cell is very important. By using a cylindrical cell with a small diameter compared with the wavelength of the sound, the propagation of the wave will mainly be parallel to the length of the cell. This is of great importance because the propagation then can be treated as one-dimensional, and the first order wave equation can be applied [41].

In accordance with the object of the present invention there is provided a means for increasing sensitivity in electrochemical analysis that involves a redox reaction at an electrode surface, including an analysis cell, a system of electrodes arranged in an analysis cell filled with a solution to be analysed producing a measuring signal as a consequence of a redox reaction at the electrodes, wherein the measuring signal is a measure of the concentration of a metal in the solution. The means of the invention is characterized in that it comprises a sound source arranged for generating sound waves in the frequency range 20 to 1000 Hz and located in or adjacent to the analysis cell for producing sound waves therein, thereby increasing the mass transport to the electrode surfaces and hence increasing the measuring signal without simultaneously increasing the noise level.

In a preferred embodiment of the invention the sound source is arranged for generating low frequency sound waves, and the sound waves may have a frequency of about 100 Hz. In another embodiment the sound source may be arranged for generating sound waves with mainly one frequency or with several frequencies. The sound source may also be arranged for generating sound waves creating standing waves in the analysis cell. Also, the sound source may be arranged for generating sound waves putting the electrodes into resonance.

In a further embodiment the analysis cell may be cylinder shaped, and may have a cross-sectional diameter which is small compared to the sound wavelength, the sound waves mainly propagating in parallel with the longitudinal direction of the analysis cell.

The present invention further concerns a method for increasing the sensitivity in measurements when performing electrochemical analysis that involves a redox reaction at an electrode surface, wherein a system of electrodes is arranged in an analysis cell filled with a solution to be analysed, and a measuring signal being produced by the electrodes as a consequence of a redox reaction at the electrodes, wherein the measuring signal is a measure of the concentration of a metal in the solution. The method of the invention is characterized in that it comprises generating sound waves in the frequency range 20 to 1000 Hz in the analysis cell during measurements by means of a sound source which beforehand is arranged in or adjacent to the analysis cell, for increasing the mass transport to the electrode surfaces and thereby increase the measuring signal without simultaneously increasing the noise level.

In a preferred embodiment of the invention the sound source generates low frequency sound waves, and the sound waves may have a frequency of about 100 Hz. In another embodiment the sound source may generate sound waves with mainly one frequency or with several frequencies. The sound source may also generate standing waves in tee analysis cell. Also, the sound source may generate sound waves putting the electrodes into resonance.

Another aspect of the invention concerns a use of the method and the means described above in trace analysis of heavy metals, like e.g. Zn. Cd, Pb and Cu.

A further aspect of the invention concerns a use of the method and the means described above in voltammetric analysis, and the voltammetric analysis may be of the type differential pulse anodic stripping voltammetry.

BRIEF DESCRIPTION OF THE DRAWINGS

Embodiments of the invention shall now be described in detail with reference to the accompanying drawings, where.

DETAILED DESCRIPTION OF THE INVENTION

Figure 1A:
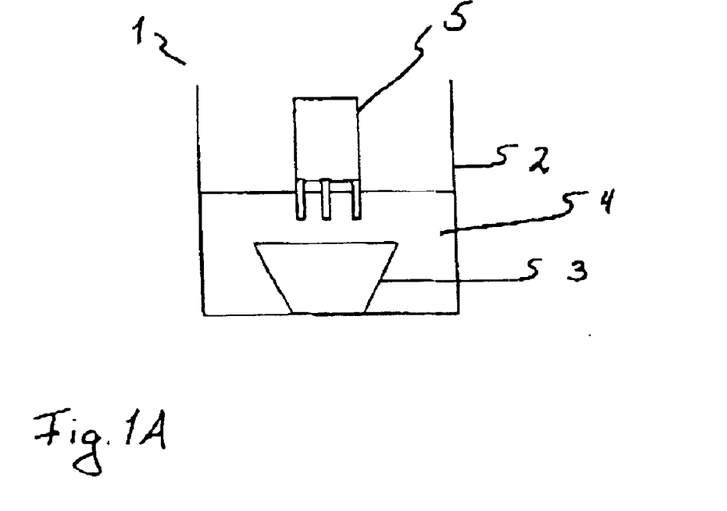
FIG. 1A is a side view of an apparatus according to an embodiment of the present invention.
Figure 1B:
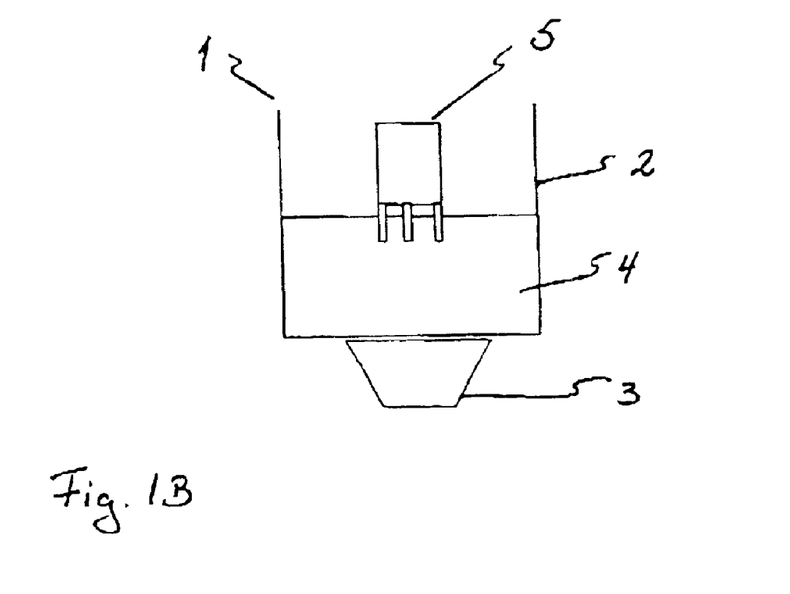
FIG. 1B is a side view of an apparatus according to an embodiment of the present invention.

FIG. 1A depicts a voltammetric analysis system 1 consisting of a cylindrical glass cell 2 (analysis cell), a loudspeaker 3 in a solution 4, and an electrode system 5 with three electrodes. The loudspeaker 3 is put into the solution in FIG. 1, but it can also be located in or adjacent to the wall of the glass cell 2 or arranged in other suitable ways for generating sound waves in the analysis system. FIG. 1B depicts a voltammetric analysis system 1 with the loudspeaker 3 located adjacent to the wall of the glass cell 2. Means for applying a voltage signal to the electrode system and for collecting the current signal are not shown in FIGS. 1A and 1B.

The experiments were carried out using an EG & G Parc 264A Polarographic Analyzer with an EG & G Parc 303A Static Mercury Drop Electrode and an EG & G Parc 305 Stirrer (Princeton Applied Research, Princeton, N.J. 08540, U.S.A.). Otherwise stated, standard 10 ml standard glass cells were used.

Potentials were measured vs. a silver/silver chloride/saturated silver chloride/saturated potassium chloride reference electrode, using a three-electrode system as shown in FIG. 1A. The third electrode was a platinum wire. The instrument was connected to a personal computer via a PC-30 multifunction board (Intel Corporation, Santa Clara, Calif. 95051, U.S.A.) (not shown in FIG. 1A) for data acquisition, calculation and presentation, as discussed in a previous paper [2].

The solution 4 in the voltammetric cell 2 was exposed to stirring with a magnetic stirrer, or by using the vibration from a commercial electric toothbrush. Alternatively, the stirrer was replaced with miniature piezoelectric buzzers 3 (miniature loudspeakers) in the solution 4, using several amplitudes and frequencies. Using an adjustable propeller stirrer made in our laboratories also performed several attempts of controlled stirring.

The voltammetric cell was exposed to sound by using a 20 W Fabr Audax AT080MO (ELFA S17117 SOLNA, SWEDEN) broad band loudspeaker, with a wide frequency range (55 Hz–20 kHz). This enabled one to investigate in the entire audible sound spectrum as well as somewhat outside that range. This loudspeaker was placed in a water tight inert rubber balloon in the bottom of an inert plastic beaker, to be used as the voltammetric cell. The loudspeaker was connected to a CREATIVE Sound Blaster 32 PnP PC Sound Card. The commercial computer program CoolEdit96 (Syntrillium Software Corporation, P.O. Box 62255, Phoenix, Ariz. 85082-2255, USA) was used to generate preferred sound frequencies and amplitudes.

The purity of mercury is essential. Mercury "pa. 4403 for polarography", E. Merck. Darmstadt, BRD was found to be satisfactory. Norsk Hydro, Norway, supplied oxygen free nitrogen gas. The water was purified by using an ELG-ASTAT OPTION 4 Water Purification Equipment (Elga Ltd. Bucks, UK). All the remaining reagents were of analytical reagent grade quality.

All the voltammetric experiments were performed as Anodic Stripping Voltammetry (DPASV) of heavy metals, with different exposure to stirring, vibration and sound, during the various parts of the sequences. Other modes of voltammetric techniques have not been investigated in the present work, this because the effects are assumed to behave very similar.

For practical reasons, the present sound experiments had to be carried out by using a larger volume of the voltammetric cell than the standard one. A 1000 ml plastic beaker was used for that purpose, with the loudspeaker in a watertight balloon at the bottom of the beaker about 1.0 cm from the electrode surface. The effect of the applied sound was about 5 W. Single frequency sound was mainly applied, but composite sound with more than one single frequency in the range 40 to 2000 Hz was also investigated.

Figure 2:
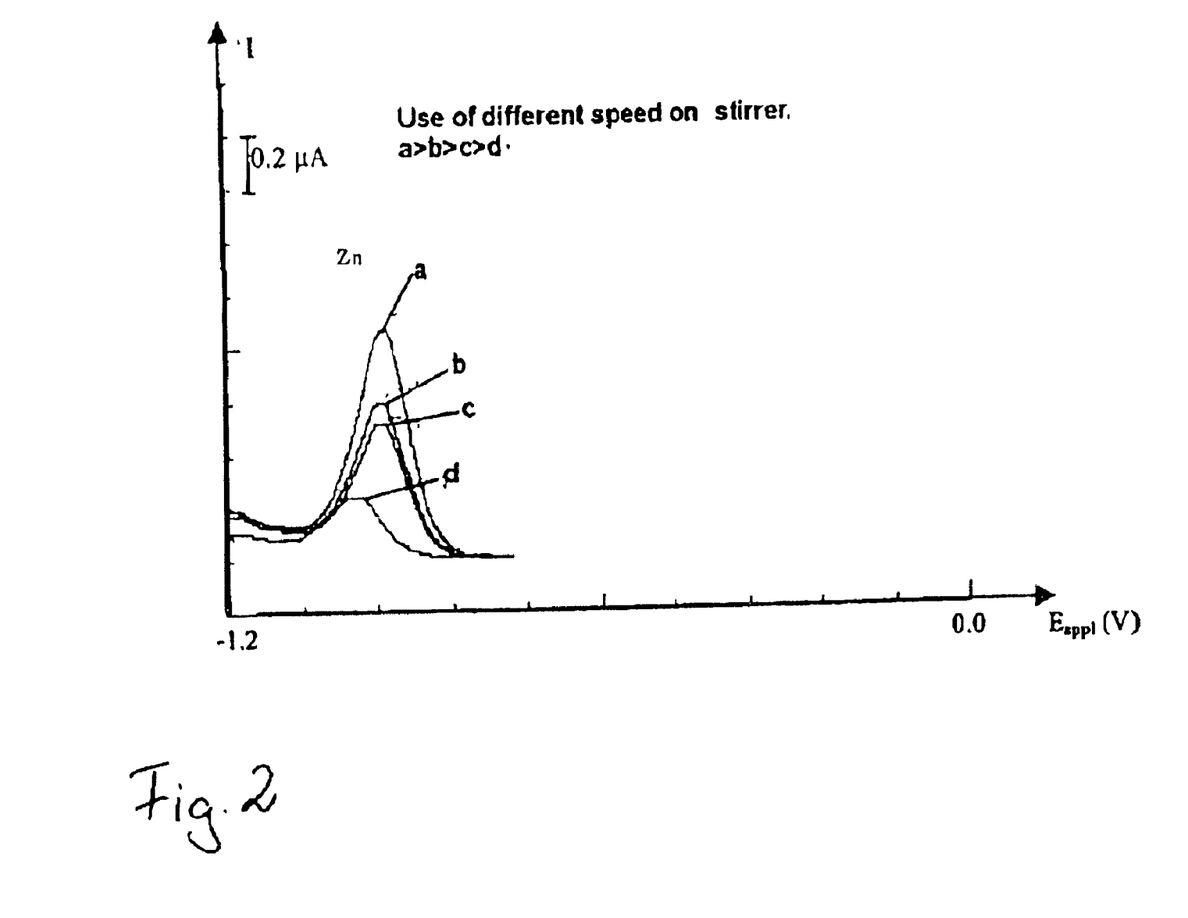
FIG. 2 is a graph showing the effect of the rotation frequency of a mechanical stirrer on the measuring signal.

The effect of the rotation frequency of the mechanical stirrer is shown in FIG. 2 for solutions of zinc ions. FIG. 2 shows voltammetric curves where the resulting current (I) is a function of applied potential (voltage, $E_{appl}(V)$) between the working and reference electrode. Graph a represents the highest frequency used and graph d represents the lowest frequency used (a>b>c>d). The stirring was only performed during the deposition step in each experiment. The highest frequency used (graph a) is similar to the fastest able rotation frequency of the magnetic stirrer. As found from the figure, the magnitude of the signal increases substantially with higher rotation frequencies.

In FIG. 2 the DPASV analysis was carried out in a 100 ppb zinc in 0.1 M KCl solution. The concentration of supporting electrolyte was 0.1 M KCl, the deposition time 120 s, the scan rate, 5 mV/s, and pulse height 25 mV.

Figure 3:
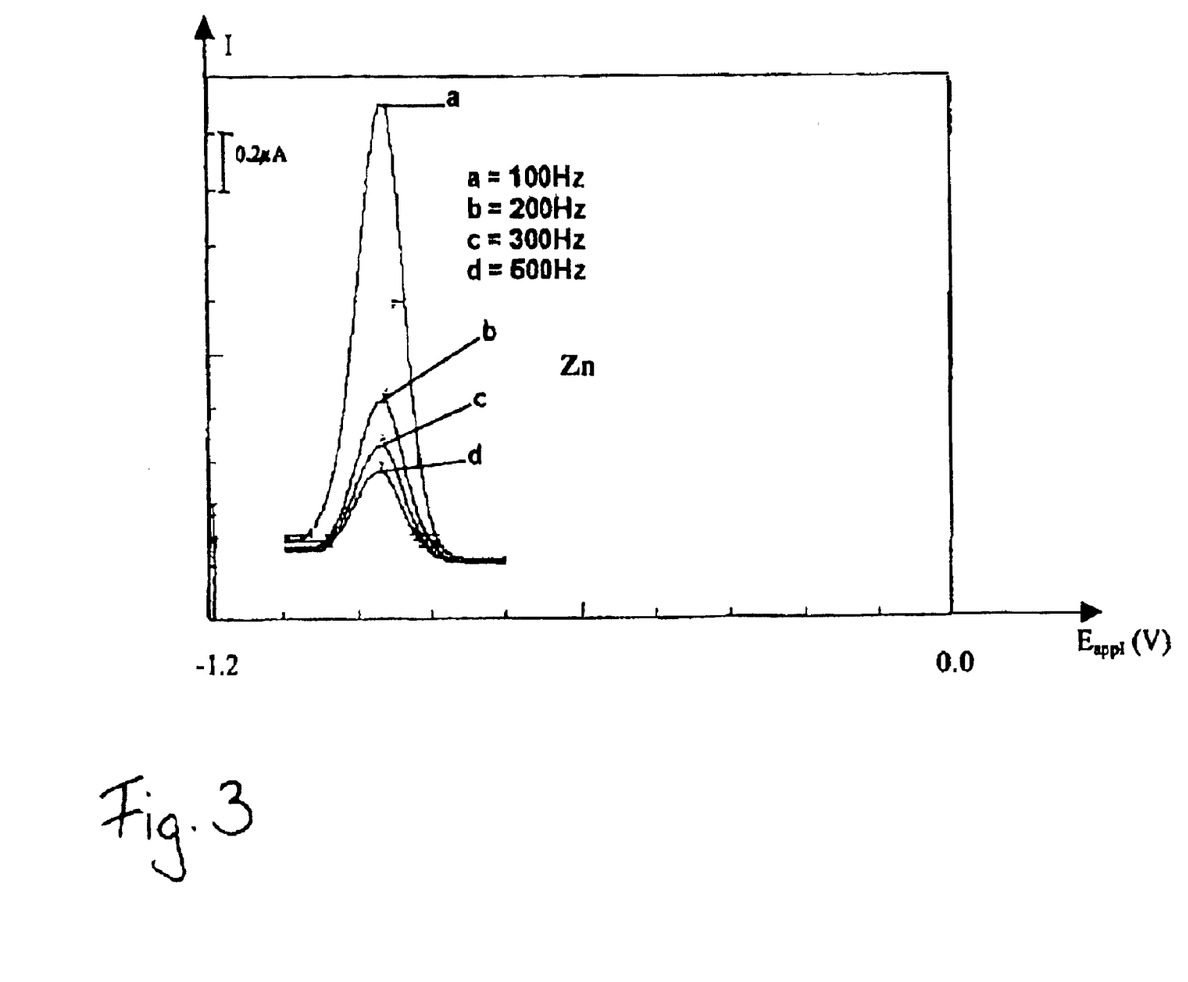
FIG. 3 is a graph showing the effect of sound exposure with different frequencies on the measuring signal according to the present invention.

The most interesting experience is the effect of exposure of sound of different frequencies. The sound was applied during all the sequences of each experiment. The results of exposure to sound of different frequencies for solutions of zinc ions are given in FIG. 3. FIG. 3 shows voltammetric curves where the resulting current (I) is a function of applied potential (voltage, $E_{appl}(V)$) between the working and reference electrode. Graph a is the result when using sound with a frequency of 100 Hz, in graph b the frequency was 200 Hz, in graph c the frequency was 300 Hz and in graph d the frequency was 500 Hz. In FIG. 3 the DPASV analysis was carried out in a 100 ppb zinc in 0.1 M KCl solution. The concentration of supporting electrolyte was 0.1 M KCl, the deposition time 120 s, scan rate 5 mV/s, and pulse height 25 mV.

For experimental reasons, sound with frequencies lower than about 85 Hz is difficult to apply using a loudspeaker system, and some mechanical devices as alternative sources for very low frequency sound has to be used [42] which indicated that the optimum frequency is about 85 Hz. This indicates that an optimum frequency of the sound gives a substantial increase of the signal.

As expected, in a qualitative way only, an increase of the amplitude of the sound also increase, the signal, leading to that the plot going off scale.

Figure 4:
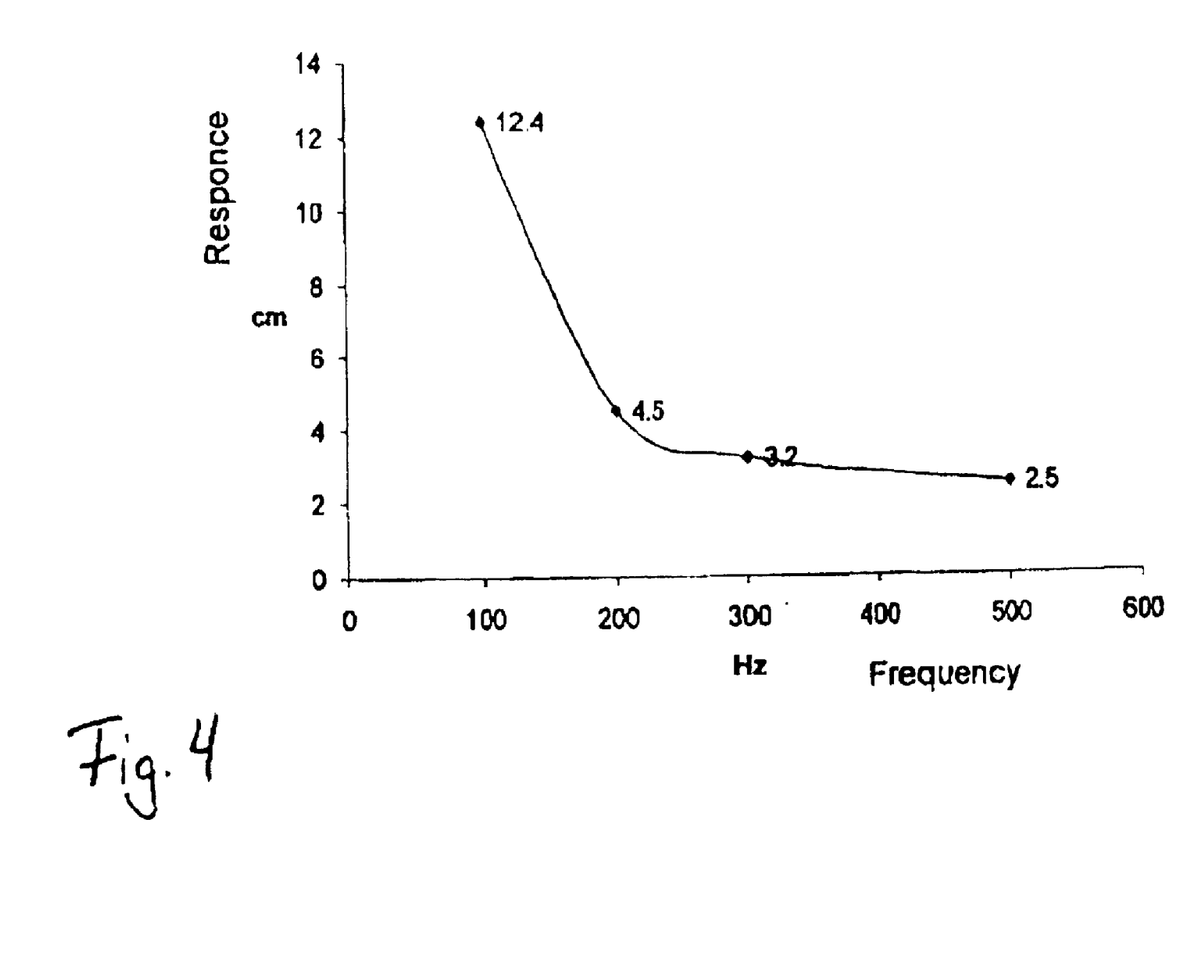
FIG. 4 is a graph showing the response vs. frequency of the exposed sound for a solution with zinc ions according to the present invention.

The response (peak current) vs. the frequency (Hz) of the exposed sound for a solution with zinc ions is given in FIG. 4.

Table 1 gives results from sound exposure and the use of the propeller stirrer for zinc, cadmium and lead ions. Finally a part of the solutions were transferred to the cell with the magnetic stirrer for comparative measurements.

In table 1 the peak current for zinc, cadmium and lead is given in cm+standard deviation. The DPASV analysis was carried out in a 150 ppb zinc, cadmium, and lead solution. The concentration of supporting electrolyte was 0.1 M KCl, the deposition time 120 s, the scan rate 5 mV/5, and pulse height 25 mV. Five repetitions were performed.

TABLE 1

| Element | Propeller [cm] | Sound (different frequencies) [cm] |
|---|---|---|
| Zn | 7.6 ± 1.11 | 14.3 ± 0.17 |
| Cd | 2.6 ± 0.30 | 9.2 ± 1.27 |
| Pb | 2.4 ± 0.32 | 6.6 ± 10.49 |

By comparing the results from sound exposure and by using the propeller stirring system, a gain of 87%. 248% and 183% in favour of sound exposure was obtained for measurements of zinc, cadmium and lead, respectively.

Corresponding comparison of sound exposure vs. the use of ordinary magnetic stirrer was 88%, 284% and 315% in favour of sound exposure of the same elements.

The experiments above were carried out using a mixed sound containing different frequencies, with the lowest value of 40 Hz and highest about 2000 Hz. However, for experimental reasons, the duration of the sound was limited to 84 seconds, and restarting was required during the process. This can explain the high value (13.8%) of the standard deviation for cadmium.

Experiments were also performed with non-composite frequency sound of 85 Hz, this being close to the expected optimum frequency. The results are given in table 2.

In table 2 the peak height for zinc is given in cm±standard deviation. The DPSV analysis was performed in a 150 ppb zinc solution and the concentration of the supporting electrolyte was 0.1 M KCl, deposition time 120 s, scan rate 5 mV/s. and pulse height 25 mV. Five repetitions were performed.

TABLE 2

| Propeller stirrer [cm] | Sound (85 Hz) [cm] | Percent Enhancement |
|---|---|---|
| 3.5 ± 0.56 | 9.6 ± 0.30 | 172 |

In order to investigate the reproducibility of sound exposed systems, some parallel investigations were performed. The results are shown in table 3.

In table 3 the peak height is given in $\mu A$. The DPSV analysis was performed in a 160 ppb zinc solution. The concentration of supporting electrolyte was 0.1 M KCl, deposition time 120 s, scan rate 5 mV/s, and pulse height 25 mV. Four repetitions were performed.

TABLE 3

| Element | Average peak height [$\mu A$] | Percent standard deviation |
|---|---|---|
| Zn | 0.574 ± 0.022 | 3.8 |
| Cd | 0.438 ± 0.007 | 1.6 |
| Pb | 0.786 ± 0.012 | 1.5 |

Figure 5:
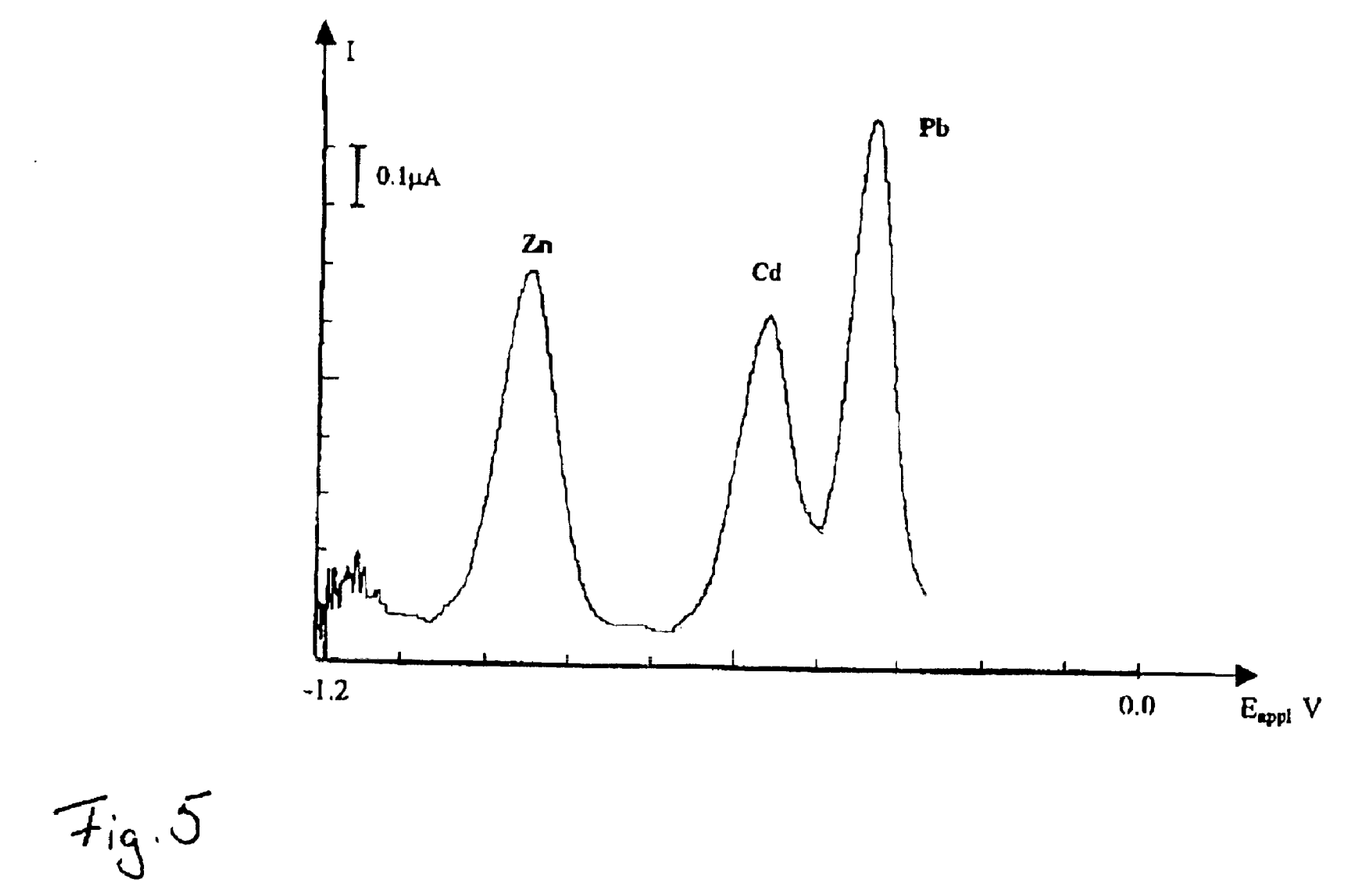
FIG. 5 is a graph showing a plot of a typical voltammetric curve for a system exposed to audible sound according to the present invention.

A typical voltammetric curve for a system exposed to audible sound is given in FIG. 5. In FIG. 5 the graph shows the resulting current (I) as a function of applied potential (voltage, $E_{appl}(V)$) between the working and reference electrode. In FIG. 5 the different peaks represent respectively Zn, Cd and Pb. The DPSV analysis was performed in a 160 ppb zinc solution. The concentration of supporting electrolyte was 0.1 M KCl, the deposition time 120 s, scan rate 5 mV/s, and pulse height 25 mV. The sound was applied during all the sequences in the experiment.

For comparison, results from six parallels of the similar system, using conventional magnetic stirring are given in table 4.

In table 4 the peak height is given in $\mu A$ from a usual magnetic stirred solution. DPSV analysis was performed in a 100 ppb zinc, cadmium, and lead solution. The concentration of supporting electrolyte was 0.1 M KCl, deposition time 120 s, scan rate 5 mV/s, and pulse height 25 mV. Four repetitions were performed.

TABLE 4

| Element | Average peak height [$\mu A$] | Percent standard deviation |
| --- | --- | --- |
| Zn | 0.470 ± 0.024 | 5.1 |
| Cd | 0.198 ± 0.008 | 4.1 |
| Pb | 0.379 ± 0.037 | 9.7 |

In order to ensure that the sole presence of the loudspeaker system did not effect the results; some test experiments were carried out. Some results are given in table 5 for measurements with cadmium and lead.

In table 5 the test experiments were carried out to ensure that the sole presence of the loudspeaker system did not affect the results. DPSV analysis was performed in a 100 ppb cadmium and lead solution. The concentration of the supporting electrolyte was 0.1 M KCl, the deposition time 120 s, scan rate 5 mV/s, and pulse height 25 mV.

TABLE 5

| Element | Peak height Magnetic stirring [$\mu A$] | Peak height No stirring at all [$\mu A$] | Peak height No stirring, but the loudspeaker in the solution. [$\mu A$] |
| --- | --- | --- | --- |
| Cd | 1.62 | 0.24 | 0.18 |
| Pb | 0.86 | 0.14 | 0.18 |

These results conclude that the presence of the loudspeaker did not effect the results.

The initial experiments using simple mechanical stirring during the deposition part of stripping voltammetry stated that some improvements could be obtained by substituting the magnetic stirrer with vibration devices. However, the great difference between the exposure of sound to the voltammetric cell compared with the use of magnetic or propeller stirring is that no stirring can be used during the registration step except from the sound exposure for reasons of reproducibility.

In stripping voltammetry, any agitation can be used during the deposition sequence. The present results indicate that pure mechanical agitation and sound exposure, as well as a combination give quite similar effects. However, in the scanning sequence, where sound is the only acceptable interaction, a very pronounced improvement of the signal is achieved. Consequently the sound exposure can be performed during all the sequences of stripping voltammetry, and with no real need for additional stirring during the deposition.

In the present investigation, differential pulse anodic stripping voltammetry is the only technique being used. However, other modes of voltammetry are assumed to behave similarly.

It is reasonable to assume that all voltammetric signals in general will be increased by sound exposure. However, with the stripping techniques, the peaks with the most positive potentials are relatively more increased, compared with the traditional method with a magnetic stirrer being used during the deposition only. This can be explained from the fact that the first part of the scanning with sound exposure also involves a significant deposition. Accordingly, no deposition sequence should actually be needed when sound exposure is used. This has not at present been studied in our laboratories, but obviously this will substantially facilitate the instrumentation and the application of stripping voltammetry for trace analyses in addition to the obtained gain of sensitivity.

The configuration of the cell system and the amplitude of the sound are obviously of great importance for optimum results. Resonance and standing waves give most favourable results, and obviously more than one resonance frequency can be present. It is assumed that the electrode system is under steady state conditions with certain exposure of sound. Attempts to verify this experimentally, as well as from mathematical modelling are now being carried out in our laboratories.

It is concluded that the lowest frequencies investigated give the most optimal gain of the signal. For experimental reasons, sound with frequencies lower than about 85 Hz is difficult to apply to the cell system using a loudspeaker system. Lower frequencies are at present being investigated in our laboratories by applying some mechanical devices as alternative sources for very low frequency sound. These experiments also indicate an optimum of about 85 Hz [42]. Due to the simplicity of generating sound by a loudspeaker via the multimedia equipment of a computer, this technique is preferred for experimental reasons.

In conclusion it is also slated that modulation in voltammetry by using low frequency sound is simple to carry out experimentally, and this gives favourable improvements by increasing the sensitivity without a corresponding increase of the level of the noise. This can mainly be explained by an increase of the transport of mass to the electrode surface. Further it is assumed that this effect is most pronounced in case of acoustic resonance and when standing waves appear. This increase of mass transport has only been investigated with the technique of DPASV in the present initial investigation. However, it is reasonable to assume that corresponding effects will appear using other modes of voltammetry.

Different kinds of measuring electrode material can be used with the present invention, but also with voltammetric analysis systems in general, e.g. mercury drop, mercury film, solid metals, carbon, liquid and solid amalgams. Solid amalgams, somewhat similar to the amalgam used by dentists, are promising due to 1) the high overpotential for hydrogen reduction, as this allows a wide measuring range, and 2) the low toxicity of such materials compared with mercury.

Differential pulse anodic stripping voltammetry is particularly important in trace analysis of heavy metals like e.g. zinc, copper, cadmium and lead. Also, voltammetric analysis methods are cheap, suitable for online systems and may be used in continuous environmental monitoring.

REFERENCES

[1] K. H. Schrøder, J. Electroanal. Chem., 1988, 246, 15.
[2] A Hannisdal and K. H. Schrøder, J. Electroanal. Chem., 1989, 263, 23.
[3] Jesus Galvez and K. H. Schrøder, J. Electroanal. Chem., 1993, 361, 121.

[4] Ricardo D. Riso, Philippe Monbet, Pierre Le Corre, Analyst, 1997, 122, 1593.

[5] F. M. Matysik, S. Matysik, A. M. O. Brett. C. M. A. Brett, Analytical Chemistry, 1997, 69, 1651.

[6] J. Cassidy, D. Mullen, P. Cullen, Electroanalysis, 1996, 8, 918.

[7] Y I Turyan, Talanta, 1997, 44, 1.

[8] M. E. R. Dam, K. N. Thomsen, P. G. Pickup and K. H. Schrøder, Electroanalysis, 1995, 7, 70.

[9] Maria E. R. Dam and Knut H. Schrøder, Electroanalysis, 1996, 8, 1040.

[10] N. A. Madigan, T. J. Murphy, J. M. Fortune and C. R. Louis A. Coury, Jr. Anal. Chem., 1995, 67, 2781.

[11] C. R. S. Hagan and Louis A. Coury, Jr., Anal. Chem., 1994, 66, 399.

[12] R. G. Compton and F. M, Matysik, Electroanalysis, 1996, 8, 218.

[13] H. Zhang and Louis A. Coury, Jr., Anal. Chem., 1993, 65, 1562.

[14] J. Klima, C. Bernard and C. Degrand, J. Electroanal. Chem., 1994, 367, 297.

[15] R. G. Compton, J. C. Eklund, S. D. Page, G. H. W. Sanders and J. Booth, J. Phys. Chem., 1994, 98, 12410.

[16] H. D Dewald and B. A. Peterson, Anal. Chem., 1990, 62, 782.

[17] Joseph Wang, Analytical Electrochemistry, VCH Publishers Inc., New York 1994.

[18] R. G. Compton, J. C. Eklund and S. D. Page, J. Appl. Electrochem., 1996, 26, 775.

[19] T. J. Mason, Sonochemistry: The Use of Ultrasound in Chemistry. The Royal Society of Chemistry, Cambridge 1990.

[20] P. R. Birkin and S. Silvia-Martinez, J. Chem. Soc, Chem. Commun, 1995, 1807.

[21] F. Marken, R. G. Compton, S. G. Davies, S. D. Bull, T. Thiemann, M. Luisa Sá e Melo, A. Campos Neves, J. Castillo, C. Gisèle Jung, and A. Fontand, J. Chem. Soc., Perkin Trans. 2, 1997, 2059.

[22] F. Albertus, A Llerena, J. Alpizar, V. Cerda, M. Luque, A. Rios, M. Valcarcel, Analytica Chimica. Acta, 1997, 355, 1, 22

[23] M. Hepel, X. M. Zhang, R. Stephenson, S. Perkins, Microchemical Journal, 1997, 56, 1, 79.

[24] J. Labuda, M. Buckova, L. Halamova, Electroanalysis, 1997, 9, 14, 1129.

[25] H. P. Nirmaier, G. Henze, Electroanalysis, 1997, 9, 6, 619.

[26] F. Prieto, W. J. Aixill, J. A. Alden, B. A. Coles, R. G. Compton, Journal of is Physical Chemistry B, 1997, 101, 28, 5540.

[27] J. C. Ball, J. A. Cooper, R. G. Compton, Journal of Electroanalytical Chemistry, 1997, 435, 1–2, 229.

[28] C. F. Bobes, M. T. Fernandez-Abedul, A. Costa-Garcia, Electroanalysis, 1998, 10, 10, 701

[29] Joseph Wang, B. Tian, Jianyan Wang, Analytical Communications, 1998, 36, 241.

[30] Jarbas J. R. Rohwedder, C. Pasquini, Analyst, 1998, 123, 1641.

[31] P. R. Birkin, S. Silvia-Martinez, Ultrasonics Sonochemistry, 1997, 4, 2, 121.

[32] A. M. O. Brett, F. M. A. Brett, F. M. Matysik, S. Matysik, Ultrasonics Sonochemistry, 1997, 4, 2, 123.

[33] A. M. O. Brett, F. M. Matysik, Ultrasonics Sonochemistry, 1997, 4, 2, 125.

[34] C. G. Jung, F. Chapelle, A. Fontana, Ultrasonics Sonochemistry, 1997, 4, 2, 117.

[35] C. Agra-Gutièrrez, R. G. Compton, Electroanalysis, 1998, 10, 3, 204.

[36] R. P. Akkermans, J. C. Ball, F. Marken, R. G. Compton, Electroanalysis, 1998, 10, 1, 26.

[37] C, Agra-Gutièrrez. R. G. Compton. Electroanalysis, 1998, 10, 9, 603.

[38] D. E. Williams, K. Ellis, A. Colville, S. J. Dennison, G. Laguillo and J. Larsen, J. Electroanal. Chem., 1997, 432, 159.

[39] C. Agra-Gutièrrez, J. C. Ball, R. G. Compton, Journal of Physical Chemistry B, 1998, Vol 102, Iss 36, pp 7028–7632.

[40] Sears, Zemansky and Young, University Physics. 7.th ed., Addison-Wesley, Canada 1987, Chap. 12, 13, 21, 22, 23.

[41] Philip M. Morse and K. Uno Ingard, Theoretical Acoustics, McGraw-Hill, 1968, Chap. 6.

[42] K. Sveinhaug and K. Schrøder, Unpublished results.

What is claimed is:

1. A system for increasing sensitivity in an electrochemical analysis, said system comprising:

an analysis cell;

a plurality of electrodes arranged in said analysis cell;

wherein said analysis cell is filled with a solution to be analyzed, wherein a measuring signal is produced as a consequence of a redox reaction at the electrodes, wherein the measuring signal is a measure of a concentration of a metal in the solution, wherein a sound source is arranged for generating sound waves in a frequency range of 20 to 1000 Hz, wherein the sound source is located in or adjacent to the analysis cell for producing sound waves therein, and wherein the production of sound waves increases a mass transport to the electrodes so as to increase the measuring signal without simultaneously increasing a noise level.

2. The system according to claim 1, wherein the sound source is arranged for generating sound waves with a frequency of about 100 Hz.

3. The system according to claim 1, wherein the sound source is arranged for generating sound waves with mainly one frequency.

4. The system according to claim 1, wherein the sound source is arranged for generating sound waves with several frequencies.

5. The system according to claim 1, wherein the sound source is arranged for generating sound waves creating standing waves in the analysis cell.

6. The system according to claim 1, wherein the sound source is arranged for generating sound waves putting the electrodes into resonance.

7. The system according to claim 1, wherein the analysis cell has a cylindrical shape.

8. The system according to claim 7, wherein the analysis cell has a cross-sectional diameter which is small compared to a wavelength of the sound waves such that the sound waves mainly propagate in parallel with a longitudinal direction of the analysis cell.

9. A method for increasing sensitivity in measurements when performing an electrochemical analysis, wherein a plurality of electrodes are arranged in an analysis cell filled with a solution to be analyzed, wherein a measuring signal is produced by the electrodes as a consequence of a redox reaction at the electrodes, and wherein the measuring signal is a measure of a concentration of a metal in the solution, said method comprising:

generating sound waves in a frequency range of 20 to 1000 Hz in the analysis cell during measurements by a sound source which is arranged in or adjacent to the analysis cell, wherein said generating sound waves in the frequency range of 20 to 1000 Hz increases a mass transport to the electrodes so as to increase the measuring signal without simultaneously increasing a noise level.

10. The method according to claim 9, wherein the sound source generates sound waves with a frequency of about 100 Hz.

11. The method according to claim 9, wherein the sound source generates sound waves with mainly one frequency.

12. The method according to claim 9, wherein the sound source generates sound waves with several frequencies.

13. The method according to claim 9, wherein the sound source generates standing waves in the analysis cell.

14. The method according to claim 9, wherein the sound source generates sound waves putting the electrodes into resonance.

15. The system according to claim 1, wherein the system is used in trace analysis of heavy metals.

16. The system according to claim 15, wherein the heavy metals comprise one of Zn, Cd, Pb, and Cu.

17. The system according to claim 1, wherein the electrochemical analysis comprises a in voltammetric analysis.

18. The system according to claim 17, wherein the voltammetric analysis is a differential pulse anodic stripping voltammetry.

19. The system according to claim 17, wherein the measuring electrode is of solid amalgam.

20. The method according to claim 9, wherein the electrochemical analysis comprises a voltammetric analysis.

* * * * *